United States Patent
Torres et al.

(10) Patent No.: US 7,071,209 B2
(45) Date of Patent: Jul. 4, 2006

(54) PROCESS FOR PREPARING A PHARMACEUTICALLY ACTIVE COMPOUND (GRANISETRON)

(75) Inventors: Salvador Puig Torres, Barcelona (ES); Pere Dalmases Barjoan, Sant Feliu de Llobregat (ES)

(73) Assignee: Laboratorios Vita, S.A., Sant Joan Despi (ES)

( * ) Notice: Subject to any disclaimer, the term of this patent is extended or adjusted under 35 U.S.C. 154(b) by 122 days.

(21) Appl. No.: 10/508,493

(22) PCT Filed: Mar. 21, 2003

(86) PCT No.: PCT/IB03/01058

§ 371 (c)(1),
(2), (4) Date: Sep. 21, 2004

(87) PCT Pub. No.: WO03/080606

PCT Pub. Date: Oct. 2, 2003

(65) Prior Publication Data

US 2005/0124650 A1 Jun. 9, 2005

(30) Foreign Application Priority Data

Mar. 26, 2002 (ES) .............................. P200200713

(51) Int. Cl.
*C07D 421/12* (2006.01)

(52) U.S. Cl. ...................................... 514/304; 546/126

(58) Field of Classification Search ................ 546/126; 514/304

See application file for complete search history.

(56) References Cited

FOREIGN PATENT DOCUMENTS

| EP | 0200444 | 11/1986 |
|----|---------|---------|
| ES | 2129349 | 2/1997 |
| WO | 9523799 | 9/1995 |
| WO | 9730049 | 8/1997 |

*Primary Examiner*—Kamal A. Saeed
(74) *Attorney, Agent, or Firm*—Wolf Block Schorr & Solis-Cohen LLP

(57) ABSTRACT

The invention relates to a process for preparing granisetron, or a pharmaceutically acceptable salt thereof, which comprises: a) cyclisation of a compound of formula (I) in an inert solvent and at a temperature between 0–100° C., in the presence of a strong acid, in order to yield the compound of formula (II); b) methylation of the compound of formula (II), with an alkylating agent, in the presence of a base, in an inert solvent and at a temperature between 0° C.–160° C., and with optional formation of a pharmaceutically acceptable salt. The process of the invention yields a granisetron of high purity, preventing impurities due to demethylation, by carrying out the methylation after rather than before cyclisation and with a higher yield.

10 Claims, No Drawings

PROCESS FOR PREPARING A PHARMACEUTICALLY ACTIVE COMPOUND (GRANISETRON)

FIELD OF THE INVENTION

This invention relates to a new process for preparing a pharmaceutically active compound. In particular, it relates to a new process for preparing granisetron and optionally obtaining a pharmaceutically acceptable salt thereof.

BACKGROUND OF THE INVENTION

The compound endo-1-methyl-N-(9-methyl-9-azabicycle [3.3.1]non-3-yl)-1H-indazole-3-carboxamide, which has been assigned the INN granisetron:

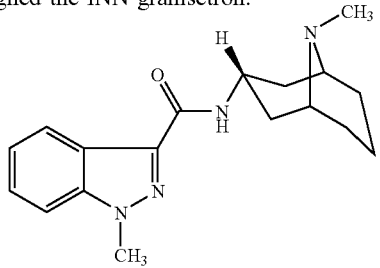

is disclosed in patent EP 200444. It acts as antagonist of 5-HT (5-hydroxytriptamine) and is useful as an anti-emetic. Said patent discloses how it is made by reaction of 1-methylindazole-3-carboxylic acid chloride with endo-3-amino-9-methyl-9-azabicycle-[3.3.1]-nonane.

Other processes for preparing granisetron were later disclosed. In patent ES 2129349 it is obtained by reaction of 1-methylindazole-3-carboxylic acid with a compound of structure (1):

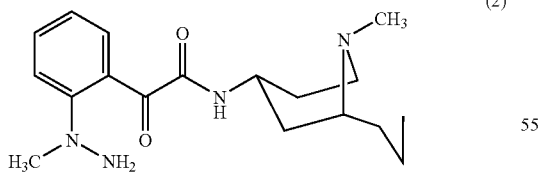

in which X represents an isocyanate group or a group that can generate an isocyanate group when heated.

International application WO 9730049 discloses an alternative process for preparing granisetron, by cyclisation of a previously methylated compound of formula (2):

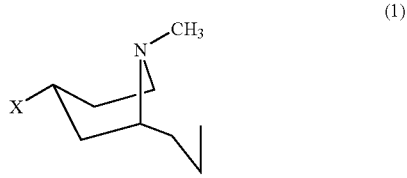

It should be noted that the methylation prior to cyclisation is carried out with sodium hydride and methyl iodide as disclosed in example 1 (b) of said international application. However, the cyclisation conditions applied to that compound of formula (2) may facilitate demethylation of the indazole N of the granisetron so obtained.

Thus, for example, examples 2 and 3 of said international application describe the cyclisation reaction, but although in Example 2 the reaction leads to granisetron, in Example 3, when the reaction time is increased under the same conditions, quantitatively demethylated granisetron is provided.

The reaction time therefore has a considerable influence on the yield values in the second step of the process, that is, in the cyclisation step, since the granisetron provided by this process contains as an impurity significant amounts of demethylated granisetron which will have to be remethylated in an additional step.

Moreover, it should not be forgotten that the methylating agent used in the methylation is methyl iodide, a carcinogenic and highly volatile compound (b.p.=41°–43° C.).

Therefore, although said international application discloses a process for preparing granisetron by methylation followed by cyclisation, it should be stressed that the yield from the last step may be very low, in which case a third step would have to be carried out, that is, a further methylation which presents the disadvantages mentioned in the preceding paragraph, in order to yield the granisetron free from demethylated granisetron.

DESCRIPTION OF THE INVENTION

The present invention provides a new process for preparing granisetron, or a pharmaceutically acceptable salt thereof, which comprises:

a) cyclisation of a compound of formula (I):

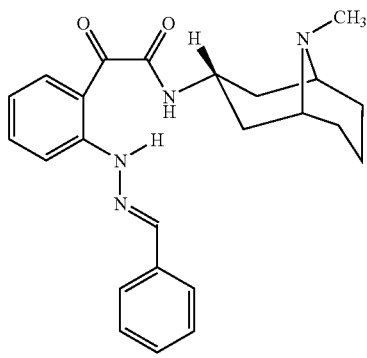

in an inert solvent and at a temperature between 0–100° C., in the presence of a strong acid, in order to yield the compound of formula (II):

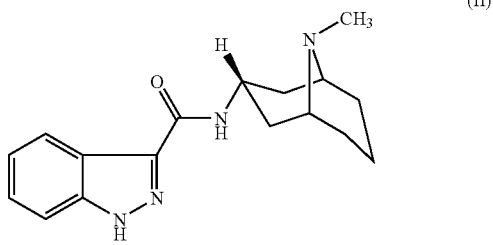

b) methylation of the compound of formula (II), with an alkylating agent, in the presence of a base, in an inert solvent and at a temperature between 0° C.–160° C., and optionally obtaining a pharmaceutically acceptable salt thereof.

The process of this invention achieves a granisetron of high purity, preventing impurities by demethylation, by carrying out the methylation after rather than before cyclisation and at the same time providing a higher yield. It should be noted, moreover, that the compounds used in the methylation do not have the disadvantages of those used in the prior art.

The cyclisation reaction is preferably carried out in a protic solvent or mixture of protic solvents, such as an alcohol, preferably methanol, or hydroalcoholic mixtures, preferably in the presence of hydrochloric acid and at a temperature between 10° and 40° C., preferably at room temperature.

In the methylation reaction the alkylating agent preferably used is dimethyl sulphate or dimethyl carbonate. Dimethyl carbonate is considered to be an ecological reagent, since its products of decomposition are methanol and carbon dioxide, while a smaller number of reaction impurities are obtained with it.

When the alkylating agent is dimethyl sulphate, the solvent preferably used is methylene chloride, toluene or tetrahydrofuran (THF) and as base sodium or potassium hydroxide in concentrated aqueous solution or in solid form. The reaction is preferably carried out in the presence of a phase-transfer catalyst, such as quaternary ammonium salts, for example TBAC.

When the alkylating agent is dimethyl carbonate, the preferable solvent used is a polar aprotic solvent such as dimethylformamide (DMF) or N-methyl-2-pyrrolidonone (NMP) and as base an alkaline carbonate, preferably potassium carbonate.

The intermediate of formula (I) can be obtained by reaction of 1-(benzylidene-amino)-1H-indole-2,3-dione (III) with endo-9-methyl-9-aza-bicyclo[3.3.1]non-3-ylamine (IV):

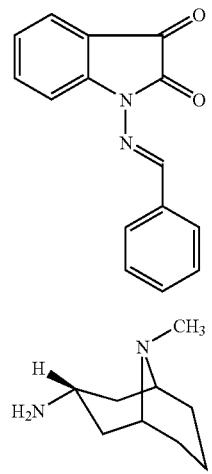

EXAMPLES OF SYNTHESIS

By way of non-restrictive explanation of the invention, the following examples are provided.

Example 1

Endo-2-[2-(N'-Benzylidene-hydrazino)-phenyl]-N-(9-methyl-9-aza-bicyclo[3.3.1]non-3-yl)-2-oxo-acetamide 29.22 grams (0.117 mol) of 1-(benzylidene-amino)-1H-indole-2,3-dione and 18 grams (0.117 mol) of endo-9-methyl-9-aza-bicyclo[3.3.1]non-3-ylamine in 250 ml of tetrahydrofuran were dissolved in a 500 ml round bottom flask and refluxed for 5 hours in an inert atmosphere. The solvent was then evaporated at reduced pressure and the oil obtained used for the next step.

Example 2

Endo-N-(9-methyl-9-aza-bicyclo[3.3.1]non-3-yl)-1H-Indazole-3-carboxamide

All the oil obtained in Example 1 was dissolved in 500 ml of methanol and 118 ml of 2 N hydrochloric acid (0.234 mol) were then added. The mixture was stirred for two hours at 20° C.–25° C. Most of the methanol was evaporated off at reduced pressure. 250 ml of ethyl acetate were added and the product extracted with 250 ml of 1 N hydrochloric acid. The combined aqueous phases were washed with 150 ml of ethyl acetate. The aqueous phase was adjusted to pH 10–11 by addition of sodium hydroxide at 10%. The solid formed was filtered and dried under vacuum, to yield 28.63 grams (82%) of the title product.

Example 3 endo-1-methyl-N-(9-methyl-9-azabicycle[3.3.1]-non-3-yl)-1H-indazole-3-carboxamide hydrochloride a) endo-1-methyl-N-(9-methyl-9-azabicycle[3.3.1]non-3-yl)-1H-indazole-3-carboxamide 2 g (6.70 mmol) of endo-N-(9-methyl-9-aza-bicyclo[3.3.1]non-3-yl)-1H-indazole-3-carboxamide, 38 ml of methylene chloride, 1.43 ml of soda 50%, 0.51 ml of water and 0.1 g of TBAC were placed in a 250 ml round bottom flask. A solution of 0.68 ml (7.10 mmol) of dimethyl sulphate dissolved in 8 ml of methylene chloride was added drop by drop for one hour, with the temperature kept at 18–22° C.

After leaving to react for 30 minutes, a check was made by TLC for disappearance of the initial product, and then 20 ml of water was added and the phases separated. The organic phase was washed with 20 ml of water.

The organic phase was evaporated to dryness to yield a residue of 2.17 g of 77.7% purity in granisetron base.

M.p.: 121–122° C. IR (cm$^{-1}$): 3420, 2920, 2860, 1670, 1530, 1495, 1285, 1210, 1130, 770, 470.

$^1$H-NMR (CDCl$_3$) (δ, ppm): 1.05 (m, 2H); 1.37 (dt, 2H); 1.52 (m, 1H); 1.96 (sc, 3H); 2.51 (s, 3H); 2.53 (m, 2H); 3.09 (d, 2H); 4.06 (s, 3H); 4.57 (m, 1H); 6.78 (d, 1H deut); 7.27 (dt, 1H); 7.39 (sc, 2H); 8.39 (d, 1H);

$^{13}$C-NMR (CDCl$_3$) (ppm): 14.3, 24.8 (2 C), 33.1 (2 C), 35.9, 40.6, 40.7, 51.2 (2 C), 108.9, 122.4, 122.7, 123.0, 126.7, 137.5, 141.2, 161.8, b) endo-1-methyl-N-(9-methyl-9-azabicycle[3.3.1]non-3-yl)-1H-indazole-3-carboxamide hydrochloride The residue was dissolved in 20 ml of IPA, and 1.1 equivalents of hydrochloric acid were added. Most of the IPA was evaporated off and 20 ml of AcOEt were added, and the precipitate dispersed, filtered and dried. A 77% yield of granisetron hydrochloride of 92% purity was obtained.

Example 4 endo-1-methyl-N-(9-methyl-9-azabicycle[3.3.1]-non-3-yl)-1H-indazole-3-carboxamide Hydrochloride 2 g (6.7 mmol) of Endo-N-(9-methyl-9-aza-bicyclo[3.3.1]-non-3-yl)-1H-Indazole-3-carboxamide, 23 ml of toluene, 2 ml of soda 50%, 0.7 ml (7.3 mmol) of dimethyl sulphate and 0.1 g of TBAC were placed in a 250 ml round bottom flask.

After leaving to react for 3 hours 30 minutes at 18–20° C. a check was made by TLC for disappearance of the initial product, and 20 ml of water were then added and the phases were separated. The organic phase was washed with 20 ml of water. The organic phase was evaporated to dryness, to yield a residue of 2.12 g of 84.1% purity of granisetron base.

The residue was dissolved in 20 ml of IPA and 1.1 equivalents of hydrochloric acid were added. Most of the IPA was evaporated off and 20 ml of AcOEt added, the precipitate dispersed, filtered and dried. A yield of 80% of granisetron hydrochloride with a purity of 94% was obtained.

Example 5 endo-1-methyl-N-(9-methyl-9-azabicycle[3.3.1]-non-3-yl)-1H-indazole-3-carboxamide Hydrochloride 2 g (6.7 mmol) of Endo-N-(9-methyl-9-aza-bicyclo[3.3.1]non-3-yl)-1H-Indazole-3-carboxamide, 38 ml of THF, 1.43 ml of sodium hydroxide 50%, 0.51 ml of water and 0.1 g of TBAC were placed in a 250 ml round bottom flask. A solution of 0.68 ml (7.1 mmol) of dimethyl sulphate dissolved in 8 ml of THF was added drop by drop for 1 hour, with the temperature held at 18–22° C.

After leaving to react for 30 minutes a check was made by TLC for disappearance of the initial product and then 30 ml of water was added, the solvent evaporated, 46 ml of toluene added, the aqueous phase separated, the organic phase washed with 20 ml of water and the phases separated. The organic phase was evaporated to dryness to yield a residue of 2.41 g of 84.7% purity granisetron base.

The residue was dissolved in 20 ml of IPA, and 1.1 equivalents of hydrochloric acid were added. Most of the IPA was evaporated off and 20 ml of AcOEt added, and the precipitate dispersed, filtered and dried. This gave an 85% yield of granisetron hydrochloride of 96% purity.

Example 6 endo-1-methyl-N-(9-methyl-9-azabicycle[3.3.1]-non-3-yl)-1H-indazole-3-carboxamide hydrochloride 46 ml of dry DMF, 2 g (6.70 mmol) of Endo-N-(9-methyl-9-aza-bicyclo[3.3.1]non-3-yl)-1H-Indazole-3-carboxamide, 3 g (21.7 mmol) of potassium carbonate and 0.86 ml (10.24 mmol) of dimethyl carbonate were placed in a 250 ml round bottom flask.

The mixture was heated to reflux for 2 hours, and a check by TLC made for disappearance of the original product. The salts were filtered, the solvent evaporated and 46 ml of toluene added. It was washed twice with water and the organic phase taken to dryness.

This yielded 1.99 g of residue, with a purity of 86% as granisetron base.

The residue was dissolved in 20 ml of IPA and 1.1 equivalents of hydrochloric acid added. Most of the IPA was evaporated off and 20 ml of AcOEt were added and the precipitate dispersed, filtered and dried. This gave an 80% yield of granisetron hydrochloride with a purity of 97%.

The invention claimed is:

1. Process for preparing granisetron, or a pharmaceutically acceptable salt thereof, which comprises:
    a) cyclisation of a compound of formula (I):

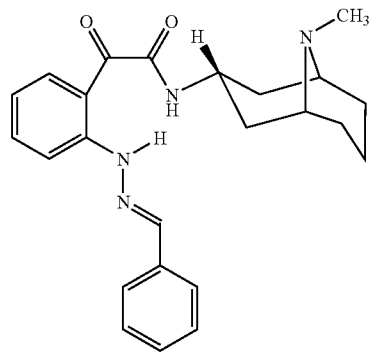

(I)

in an inert solvent and at a temperature between 0–100° C., in the presence of a strong acid, in order to yield the compound of formula (II):

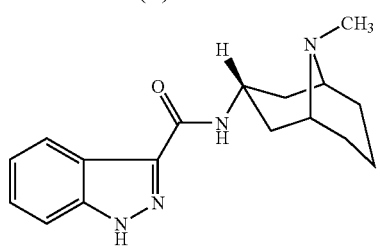

(II)

b) methylation of the compound of formula (II), with an alkylating agent, in the presence of a base, in an inert solvent and at a temperature between 0° C.–160° C. and optionally obtaining a pharmaceutically acceptable salt thereof.

2. Process as claimed in claim 1, wherein step a) is carried out in a protic solvent or mixture of protic solvents.

3. Process as claimed in claim 1, wherein step a) is carried out at a temperature between 10° C. and 40° C.

4. Process as claimed in claim 1, wherein said alkylating agent is dimethyl sulphate.

5. Process as claimed in claim 1, wherein said alkylating agent is dimethyl carbonate.

6. Process as claimed in claim 1, wherein the solvent of step b) is selected from among methylene chloride, toluene or tetrahydrofuran.

7. Process as claimed in claim 1, wherein said base is sodium or potassium hydroxide in concentrated aqueous solution or in solid form.

8. Process as claimed in claim 1, wherein step b) is carried out in the presence of a phase transfer catalyst.

9. Process as claimed in claim 1, wherein the solvent of step b) is a polar aprotic solvent selected from either dimethylformamide (DMF) or N-methyl-2-pyrrolidonone (NMP).

10. Process as claimed in claim 1, wherein said base is an alkaline carbonate.

* * * * *